United States Patent [19]

Iwakoshi et al.

[11] Patent Number: 4,844,052
[45] Date of Patent: Jul. 4, 1989

[54] APPARATUS FOR TRANSMITTING LIQUID AND GAS IN AN ENDOSCOPE

[75] Inventors: Keiichi Iwakoshi, Nasu; Mitsuru Sato, Shibuya; Hiroyuki Umeda, Kasukabe; Toshinori Nishizawa, Mitaka, all of Japan

[73] Assignees: Kabushiki Kaisha Toshiba, Kawasaki; Kabushiki Kaisha Machidaseisakujyo Bunkyo-ku, Tokyo, both of Japan

[21] Appl. No.: 167,172

[22] Filed: Mar. 11, 1988

[30] Foreign Application Priority Data

Mar. 11, 1987 [JP] Japan .................................. 62-54247

[51] Int. Cl.⁴ .............................................. A61B 1/12
[52] U.S. Cl. ...................................................... 128/4
[58] Field of Search ......................................... 128/4, 6

[56] References Cited

U.S. PATENT DOCUMENTS 4,509,507 4/1985 Yabe ........................................ 128/4

*Primary Examiner*—William H. Grieb
*Attorney, Agent, or Firm*—Foley & Lardner, Schwartz, Jeffery, Schwaab, Mack, Blumenthal & Evans

[57] ABSTRACT

An apparatus for transmitting liquid and gas in an endoscope comprising conduits for transmitting liquid and gas to an observation optical system to clean the observation optical system; and an automatic change-over device for sequentially operating both modes of the liquid and gas transmissions by turning on and off only a liquid transmitting switch disposed in an operating portion. The automatic change-over device comprises a first electromagnetic valve disposed in the liquid transmitting conduit, a second electromagnetic valve disposed in the gas transmitting conduit, a circuit for connecting the first and second electromagnetic valves to the liquid transmitting switch of the operating portion, and a control section for controlling the operations of the electromagnetic valves. When the liquid transmitting switch is turned on, the first electromagnetic valve is opened to transmit the liquid to the liquid transmitting conduit, and when the liquid transmitting switch is turned off, the first electromagnetic valve is automatically closed and the second electromagnetic valve is automatically opened to transmit the gas to the gas transmitting conduit for a constant or predetermined time.

3 Claims, 3 Drawing Sheets

4,844,052

APPARATUS FOR TRANSMITTING LIQUID AND GAS IN AN ENDOSCOPE

The present invention relates to an improved apparatus for transmitting liquid and gas through an endoscope for medical care, and, in particular, to an apparatus for easily transmitting liquid and gas in an endoscope clean and dry an end of the endoscope by reducing the of its operator.

BACKGROUND OF THE INVENTION

An endoscope is widely used to examine and care for portions of a human's body such as the duodenum, rectum, large intestine, oesophagus, ears, nose, and bladder.

An apparatus for transmitting liquid and gas through an endoscope is used to remove material attached to an observation optical system disposed at an end tip of the endoscope during the operation thereof.

Namely, when material is attached to the observation optical system during operation of the endoscope, the visual field of the endoscope is prevented so that it is necessary to remove the waste from the observation optical system by supplying liquid from a liquid transmitting path of the endoscope to a liquid transmitting nozzle disposed at an end thereof and ejecting the liquid on the observation optical system and, thereafter, supplying gas from a gas transmitting path to a gas transmitting nozzle disposed at the end of the endoscope.

The cleaning operation is indispensable and often performed in the general examination and medical care of the endoscope.

Conventionally, it is often necessary for an operator to operate liquid and gas transmitting buttons disposed in an operating portion of the endoscope during the operation thereof so as to clean the observation optical system disposed at the end of the endoscope. Accordingly, such a clearing operation is laborious for the operator, and it is desirable to simplify the cleaning operation.

In the cleaning operation by the conventional endoscope, it is necessary to (1) turn on a liquid transmitting button, (2) turn off the liquid transmitting button, (3) turn on a gas transmitting button (3), and turn off the gas transmitting button. Otherwise, it is necessary to (1) turn on the liquid and gas transmitting buttons to transmit the liquid, (2) turn on/off the liquid and gas transmitting buttons, (3) transmit the gas by closing an air leak hole on the liquid and gas transmitting buttons by a finger, and (4) turn off the liquid and gas transmitting buttons. Such sequential operations are complicated and make the operator troublesome.

SUMMARY OF THE INVENTION

To overcome the problems mentioned above, an object of the present invention is to provide an apparatus for transmitting liquid and gas in an endoscope to clean and dry an end of the endoscope by reducing the operation of an operator.

With the above object in view, an apparatus for transmitting liquid and gas in an endoscope in the present invention is provided with liquid and gas transmitting conduits for cleaning an observation optical system, and has an automatic change-over means for sequentially operating both liquid and gas transmitting modes by turning on and off a liquid transmitting button disposed in an operation portion.

In the liquid and gas transmitting apparatus of the endoscope in the present invention, both liquid and gas transmitting modes are automatically operated sequentially by only turning on and off the liquid transmitting button in the operating portion so that both liquid and gas transmitting operations can be simultaneously performed by pushing the liquid transmitting button at only one time. Accordingly, the operation of the operator is reduced and the operating efficiency in the examination and medical care by the endoscope is further improved.

BRIEF DESCRIPTION OF THE DRAWINGS

The present invention will be more apparent from the following description of the preferred embodiments thereof in conjunction with the accompanying drawings in which.

DETAILED DESCRIPTION OF THE PREFERRED EMBODIMENTS

The preferred embodiments of a liquid and gas transmitting apparatus in an endoscope in the present invention will now be described in detail with reference to the accompanying drawings.

Figure 1:
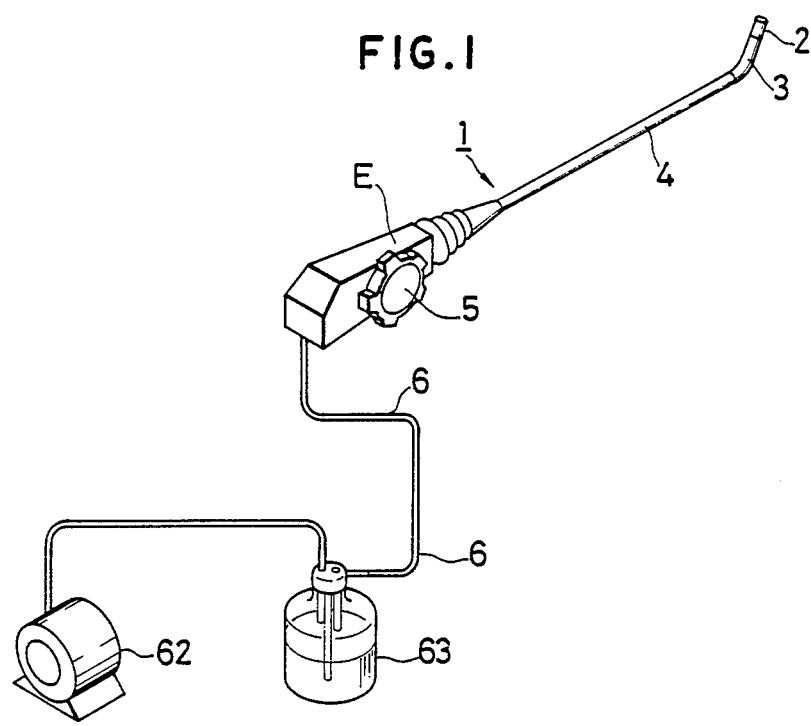
FIG. 1 is a perspective view showing a schematic construction of an apparatus for transmitting liquid and gas in an endoscope in accordance with an embodiment of the present invention.

In FIG. 1, an endoscope 1 is constituted, from an end tip to a rear end thereof, by an end portion 2 for disposing therein a charge coupled device (which is called CCD in the following description) and an observation optical system, etc., a bent portion 3 moved up, down, right and left by the operation of an operator, and a guide portion 4, and a body portion E.

The body portion E has an operating knob 5 for operating the bent portion 3, various kinds of operating buttons and a power source which are not shown, and is connected to a gas-liquid transmitting conduit 6.

Figure 2:
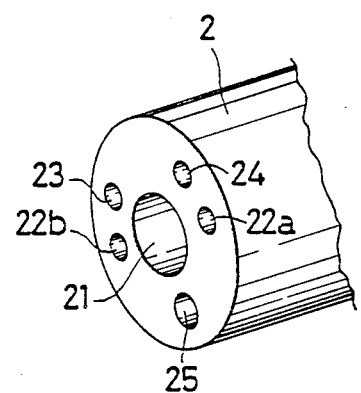
FIG. 2 is a partially enlarged perspective view of an end portion of the endoscope of FIG. 1.

The gas-liquid transmitting conduit 6 is connected at one end thereof to a liquid transmitting bottle 63 connected to a gas transmitting pump 62, and is connected at the other end to a gas transmitting nozzle 23 and a liquid transmitting nozzle 24 disposed at an end of the endoscope shown in FIG. 2.

In FIG. 2, an observation optical system 21 is constituted by a lens window having a CCD, etc., therein, and inserting ports 22a and 22b are used to receive fibers for illumination, and an inserting port 25 is used for the examination of a human's body. The gas transmitting nozzle 23 and the liquid transmitting nozzle 24 are used to remove sewage attached onto a surface of the observation optical system 21 therefrom during the operation of the endoscope, thereby cleaning the observation optical system.

In the gas-liquid transmitting apparatus of the endoscope of the present invention mentioned above, an automatic change-over device 64 is disposed in the gas-liquid transmitting conduit 6, e.g., within the body portion E, and comprises a circuitry composed of electromagnetic valves, a liquid transmitting button of an operation portion, and a control section for controlling the electromagnetic valves, as described later.

Figure 3:
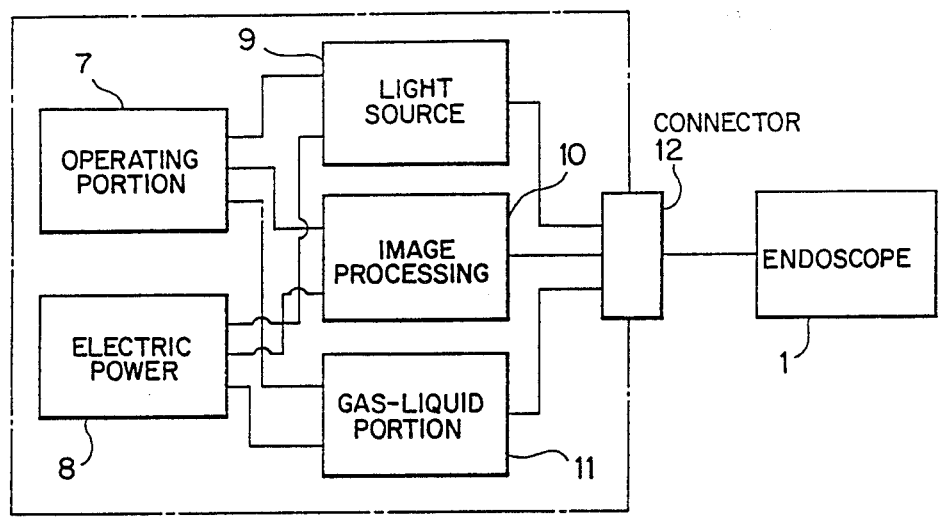
FIG. 3 is a view of a circuit of an operating portion in the endoscope.

The endoscope in the present invention is constituted by a circuit shown in FIG. 3.

Namely, in FIG. 3, an operating portion 7 and an electric power portion 8 are connected to a light source 9, an image processing portion 10 processed by CCD, and a gas-liquid portion 11. These are, in turn, connected to the endoscope 1 through a connector 12.

Figure 4:
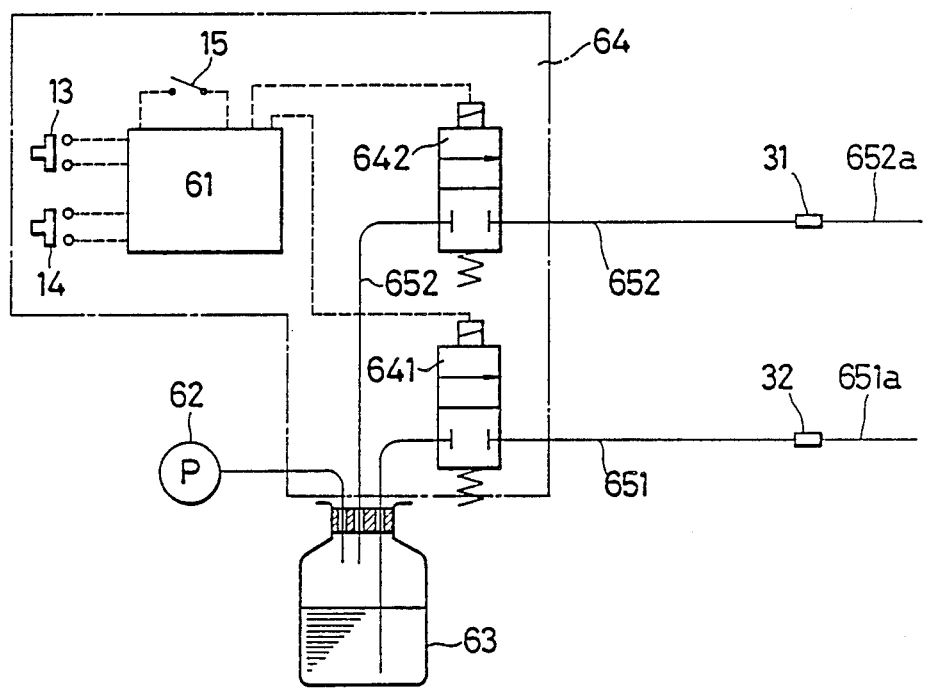
FIG. 4 is a view showing the connecting relation between conduits and a circuit indicating an automatic change-over device in the liquid and gas transmitting apparatus of the endoscope of the present invention.

As shown by dotted lines in FIG. 4, the gas-liquid portion 63 is connected to first and second electromagnetic valves 641 and 642 of the automatic change-over device 64 through a control section 61 for controlling the electromagnetic valves, which may be constituted by a CPU, logic circuits, etc.

In the automatic change-over device 64, constituting a characteristic feature of the present invention, a liquid transmitting conduit 651 and a gas transmitting conduit 652 constituting cleaning conduits are even connected at one of their ends to a liquid transmitting bottle 63 connected to a gas transmitting pump 62, and connected at the other ends to the gas transmitting nozzle 23 and the liquid transmitting nozzle 24, respectively (FIG. 2). The automatic change-over device 64 is constituted by combining the two electromagnetic valves with each other and associating the operation of these valves with the change-over operation of the liquid transmitting button 13 disposed in the electromagnetic control section 61 of the operation portion 7.

In FIG. 4, in the automatic change-over device 64, the first electromagnetic valve 641 is disposed in the liquid transmitting conduit 651, and the second electromagnetic valve 642 is disposed in the gas transmitting conduit 652. The operation of the first and second electromagnetic valves 641 and 642 is automatically performed by only the liquid transmitting button 13.

The liquid transmitting button 13 and the gas transmitting button 14 can be manually turned on and off normally to transmit only liquid or gas, but is constituted such that both the liquid and gas are automatically transmitted by operating only the liquid transmitting button 13 when the automatic gas transmitting switch 15, disposed in the electromagnetic valve control section 61 is in an automatic gas transmitting mode.

Accordingly, when the automatic gas transmitting switch 15 is turned on and the liquid transmitting button 13 is also turned on, the electromagnetic valve 641 is opened and the electromagnetic valve 642 is closed so that the liquid within the liquid transmitting bottle 63 is ejected from the liquid transmitting conduit 651 through the electromagnetic valve 641 and the liquid transmitting conduit 651a to the liquid transmitting nozzle 24 at the end of the endoscope.

When the liquid transmitting button 13 is next turned off, the electromagnetic valve 641 is automatically closed, and the electromagnetic valve 642 is automatically opened, and the gas transmitting pump 62 is operated at any time so that the gas is ejected from the gas transmitting nozzle 23 at the end of the endoscope through the gas transmitting conduit 652, the electromagnetic valve 642 and the gas transmitting conduit 652a.

Figure 5:
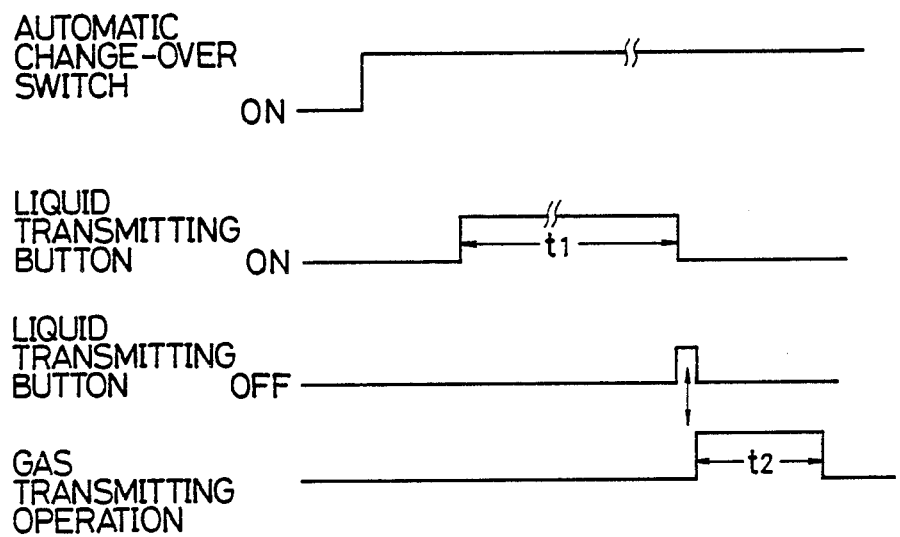
FIG. 5 is a view showing a time chart of the automatic change-over device.

A time chart of the automatic change-over device 64 is illustrated in FIG. 5.

In FIG. 5, when the automatic change-over switch 15 is turned on and the liquid transmitting button 13 is continued to be pushed for a time $t_1$ to transmit the liquid, and the liquid transmitting button 13 is thereafter turned off, the completion of the liquid transmission is detected by the circuit so that the operations of the electromagnetic valves 641 and 642 are immediately changed over. Thus, the operation of the gas transmission is next continued for a time $t_2$, and thereafter, the electromagnetic valves 641 and 642 are automatically closed, completing the operation of the apparatus.

The gas transmitting time $t_2$ can be set to be a time required in advance in the circuit, and can be arbitrarily selected and set by a dial, etc., on an operating table based on states, etc., of the thicknesses of the conduits and a diseased portion of a patient.

The automatically gas transmitting switch 15 can be constituted on the basis of a system in which commands are instructed from a keyboard.

When the automatically gas transmitting switch 15 is turned off, the ON and OFF operations of the liquid transmitting button 13 are synchronized with only the opening and closing operations of the electromagnetic valve 641, and the ON and OFF operations of the gas transmitting button 14 are synchronized with only the opening and closing operations of the electromagnetic valves 642, thereby performing the normal liquid and gas transmissions.

In the above embodiment, the liquid transmitting button 13 and the gas transmitting button 14 may be of a seesaw type instead of a push button type, and may be constituted by a two-stage type button or switch having functions of both the liquid and gas transmitting buttons 13 and 14.

The end tips of the liquid transmitting conduit 651 and the gas transmitting conduit 652 may be connected to the separate liquid transmitting nozzle 24 and gas transmitting nozzle 23, and may be connected to each other to form a single nozzle for transmitting the liquid and gas therefrom.

The above embodiment of the present invention is described in relation to the cleaning operation within the conduits during the operation of the apparatus, but the apparatus of the present invention can be used to perform the cleaning operation within the conduits after the operation of the apparatus.

As mentioned in detail in the embodiment, an apparatus for transmitting liquid and gas in an endoscope in the present invention is constituted such that both modes of the liquid and gas transmissions are sequentially operated automatically by only turning on and off a liquid transmitting button disposed in an operating portion. Accordingly, when an operator pushes the liquid transmitting button at one time, both the liquid and gas transmissions can be simultaneously performed, thereby reducing the operation of the operator and improving the operating efficiency in the examination and medical care by the endoscope.

What is claimed is:

1. An apparatus for transmitting liquid and gas in an endoscope, comprising:
   conduit means for transmitting liquid and gas to an observation optical system to clean the system; and
   automatic change-over means for sequentially operating both the liquid and gas transmission modes by turning on and off a liquid transmitting switch means disposed in an operating portion, the automatic change-over means comprising a first electromagnetic valve disposed in the liquid transmitting conduit means, a second electromagnetic valve disposed in the gas transmitting conduit means, and circuit means for connecting the first and second electromagnetic valves, the liquid transmitting switch means of the operating portion and a control section, for controlling the operation of the electromagnetic valves.

2. The transmitting apparatus of claim 1, wherein, when the liquid transmitting switch means is turned on, the first electromagnetic valve is opened to transmit liquid to the transmitting conduit means, and, when the liquid transmitting switch means is turned off, the first electromagnetic valve is automatically closed and the second electromagnetic valve is automatically opened to transmit gas to the gas transmitting means for a constant time.

3. An endoscope cleaning system, comprising:
means for supplying cleaning liquid;
means for supplying cleaning gas;
a first electromagnetic valve for controlling the supply of cleaning liquid to the optical sensing end of the endoscope;
a second electromagnetic valve for controlling the supply of cleaning gas to the optical sensing end of the endoscope;
an automatic change-over means for sequentially operating the first and second valves; and
a switch for activating the change-over means, whereby liquid is supplied to the endoscope while the switch is turned on and, upon turning the switch off, the change-over means supplies gas to the endoscope for a predetermined time.

* * * * *